United States Patent
Chung et al.

(10) Patent No.: US 7,344,836 B2
(45) Date of Patent: Mar. 18, 2008

(54) METHOD FOR NUCLEIC ACID HYBRIDIZATION USING BACK AND FORTH FLOW BETWEEN A DENATURATION CHANNEL AND A HYBRIDIZATION CHANNEL VIA A CONNECTION CHANNEL

(75) Inventors: Yung-Chiang Chung, Hsinchu (TW); Yao-Sung Chang, Hsinchu (TW); Ming-Zheng Shiu, Taichung (TW)

(73) Assignee: Industrial Technology Research Institute, Hsinchu Hsien (TW)

( * ) Notice: Subject to any disclaimer, the term of this patent is extended or adjusted under 35 U.S.C. 154(b) by 442 days.

(21) Appl. No.: 10/916,504

(22) Filed: Aug. 12, 2004

(65) Prior Publication Data

US 2005/0014185 A1  Jan. 20, 2005

Related U.S. Application Data

(62) Division of application No. 10/124,343, filed on Apr. 18, 2002, now abandoned.

(51) Int. Cl.
*C12Q 1/68* (2006.01)
(52) U.S. Cl. .......................................................... 435/6
(58) Field of Classification Search ...................... None
See application file for complete search history.

(56) References Cited

U.S. PATENT DOCUMENTS

| 6,197,595 B1 | 3/2001 | Anderson et al. |
| 6,235,471 B1 | 5/2001 | Knapp et al. |
| 6,306,598 B1 * | 10/2001 | Charych et al. ............... 435/6 |
| 6,767,706 B2 * | 7/2004 | Quake et al. .................. 435/6 |

* cited by examiner

Primary Examiner—Kenneth R. Horlick
(74) Attorney, Agent, or Firm—Birch, Stewart, Kolasch & Birch, LLP

(57) ABSTRACT

A method and apparatus designed for nucleic acid hybridization employs a hydrogen bond denaturation area with a higher temperature and a lower temperature nucleic acid hybridization area that is immobilized with nucleic acid probes. Nucleic acid-containing samples are introduced into the hydrogen bond denaturation area for heating curled nucleic acids in samples so that they become linear and are guided into the nucleic acid hybridization area. In this area, the nucleic acid hybridization rate can be multiplied by increasing the kinetic energy by the repeated flow of driven fluid. The nucleic acid hybridization apparatus provided by the invention contains a hydrogen bond denaturation area, a nucleic acid hybridization area, a two-way driving apparatus, and a temperature control element. The temperatures in the hydrogen bond denaturation area and the nucleic acid hybridization area can be maintained through the management of this temperature control element, and the fluid can gain needed kinetic energy through the two-way driving pump.

12 Claims, 2 Drawing Sheets

METHOD FOR NUCLEIC ACID HYBRIDIZATION USING BACK AND FORTH FLOW BETWEEN A DENATURATION CHANNEL AND A HYBRIDIZATION CHANNEL VIA A CONNECTION CHANNEL

This application is a Divisional of application Ser. No. 10/124,343, filed on Apr. 18, 2002 now abandoned, and for which priority is claimed under 35 U.S.C. § 120; the entire contents of all are hereby incorporated by reference.

BACKGROUND OF THE INVENTION

1. Field of the Invention

The invention generally relates to a method for nucleic acid hybridization, and specifically relates to a method and apparatus with temperature control for nucleic acid hybridization and hydrogen bond denaturation to accelerate nucleic acid hybridization.

2. Related Art

Based on rapidly developed techniques, such as PCR (polymerase chain reaction) and nucleic acid hybridization, molecular biotechnology has been gradually integrated with different areas, including material science, bioinformatics, and electronic technology, to bring about a new area of Biochips. The emergence of biochips could significantly decrease needed detection time for some diseases. For example, the initial detection time of 3-5 days by cell culture techniques can be decreased to be less than 6 hours by utilizing biochip technology.

However, such 6-hour detection time still cannot satisfy the demands of certain diseases. For instance, some diseases take less than 2 days from diagnosis to cause death. Therefore, current biochip research has been focused on shortening the needed detection time of the biochip.

To shorten the detection time, it is necessary to start from the most time-consuming technique during the test. PCR takes approximately 1.5 hours and nucleic acid hybridization takes about 4 hours. Together, these two techniques account for 92% of the whole biochip detection time. Therefore, how to shorten the amount of time consumed by these two techniques has become a key point. Presently, numerous researchers have put forth much effort on this issue, and the invention is focused on the most time-consuming nucleic acid hybridization technique.

The underlying mechanism for techniques such as Hybridization Helper is to utilize an oligonucleoride (i.e. Helper), which is complementary to the upstream or downstream region of the area where probing nucleic acid is hybridized to sample nucleic acid. Such hybridization between the nucleic acid Helper and sample nucleic acid is employed to stretch the sample nucleic acid (to eliminate the original cluttered circular conformation that is unfavorable for hybridization), which help the hybridization reaction.

In addition, another technique (called nucleic acid precipitating reagents) is available. The underlying mechanism for this technique is to utilize various buffered salt solutions to promote the sample nucleic acid precipitation at the nearby area of the probing nucleic acid. Such methodology increases the sample nucleic acid concentration in the local area to promote the processing of the hybridization reaction.

There is still another available technique called the branched oligonucleoride multimer technique, which uses probes immobilized on the surface of a chip for catching sample nucleic acid. Then, a branched oligonucleoride multimer, which is complementary to the sample nucleic acid, is linked to sample nucleic acid. Finally, fluor- or radio-labeled nucleic acid detectors are complementarily hybridized with the branched oligonucleoride multimer. Since tens or hundreds of detectors can hybridize onto a branched oligonucleoride multimer, the detection intensity can be greatly increased and the hybridization time can therefore be shortened.

Furthermore, a technique called electrically controlled hybridization takes advantage of the characteristics of negatively charged nucleic acid. By immobilizing the positive pole near the nucleic acid probe, nucleic acid in samples is lured near to the probe to make the sample nucleic acid highly concentrated in a small area and accomplish the goal of accelerating hybridization.

Another technique called volume exclusion agents employs organic molecules to form a reticular macro-structure, which can expel part of the hybridization buffer to increase the local concentration of sample nucleic acid and therefore promote the hybridization reaction.

Similar to the above technique, one technique called amphipathic hydrocarbon polymer (AHP) utilizes bipolar organic molecules (hydrophilic and hydrophobic) to form a reticular macro-structure. This macro-structure can expel part of the hybridization buffer to increase the local concentration of sample nucleic acid and therefore promote the hybridization reaction.

An apparatus called the highly parallel-integrated microfluidic biochannel array has integrated various functions, including sample pre-treatment, PCR, hybridization, washing, and signal detection. However, the hybridization rate of this apparatus has not yet been improved.

Finally, in the apparatus called the dynamic hybridization system, a nucleic acid probe is fixed on a semipermeable membrane. Meanwhile, fluid (containing sample nucleic acid) is driven by air or vacuum compression to flow towards the semipermeable membrane. Sample nucleic acids are delayed when the fluid passes through the semipermeable membrane and sample nucleic acids accumulate around the membrane to yield a higher concentration of sample nucleic acid. The hybridization rate is increased because non-complementary nucleic acid is able to pass through the holes of the semipermeable membrane.

Most of the above mentioned methods increase the hybridization rate by increasing sample nucleic acid concentration, linearlizing samples, or employing branched structure. All these hybridization accelerating methods have limitations, such as only being operable on a large scale. Nevertheless, how to speed up nucleic acid hybridization while also making the process applicable on a small scale is still the focus of a great deal of effort in research.

SUMMARY OF THE INVENTION

In order to solve the problems of the above-mentioned known techniques, this invention provides a method and apparatus designed specifically hybridization, which fulfills the aim of accelerating the nucleic acid hybridization rate by increasing kinetic energy and thermal energy of a nucleic acid-containing fluid.

Introducing a novel nucleic acid hybridization method is the other aim of this invention. By increasing the thermal energy of the nucleic acid-containing fluid, originally curled nucleic acid within the fluid is linearlized and the hybridization rate is increased.

To accomplish these aims, the invention provides a method for nucleic acid hybridization. The method includes the following steps. Firstly, a nucleic acid hybridization area is provided at first temperature, and the nucleic acid hybridization are has a channel immobilized with several nucleic acid probes. Secondly, a hydrogen bond denaturation area is provided at second temperature, and the hydrogen bond denaturation area has a second channel. The second channel is attached with a nucleic acid hybridization area, i.e. the second channel is interconnected to the first channel, to form a connection channel. Thirdly, a nucleic acids-containing fluid is guided into the connection channel. Finally, the nucleic acids-containing fluid is drove to repeatedly pass through the first channel and the second channel, i.e. flow in the connection channel back and forth.

A two-way driving apparatus, such as a two-way air-driven or fluid-driven pump, is used to drive the fluid. The fluid is retained in the first channel for the first period (such as 3 minutes) and then driven to the second channel for the second period (such as 10 seconds). While being retained in the first channel, the kinetic energy of the fluid is increased by being driven to flow back and forth.

The invention further provides a nucleic acid hybridization apparatus, including a hydrogen bond denaturation area equipped with a first channel for denaturing hydrogen bonds of nucleic acids; and a nucleic acid hybridization area equipped with a second channel, which is immobilized with nucleic acid probes. A connection channel is formed between the nucleic acid hybridization area and the first channel. A temperature control element is used for maintaining the temperature of the hydrogen bond denaturation area and nucleic acid hybridization area at the first and second temperatures, respectively. A two-way driving element is used for driving the flow of the nucleic acids-containing fluid that is infused in the connection channel.

Nucleic acid probes for hybridization can be DNA, RNA, peptide, peptide-RNA complex or derivatives of peptide-RNA complex. The temperature control element can then keep a stable temperature for the hydrogen bond denaturation area 10 and the nucleic acid hybridization area 20. The energy source can be an electric heater, microwave, laser or light.

Further scope of the applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DETAILED DESCRIPTION OF THE INVENTION

Figure 1:
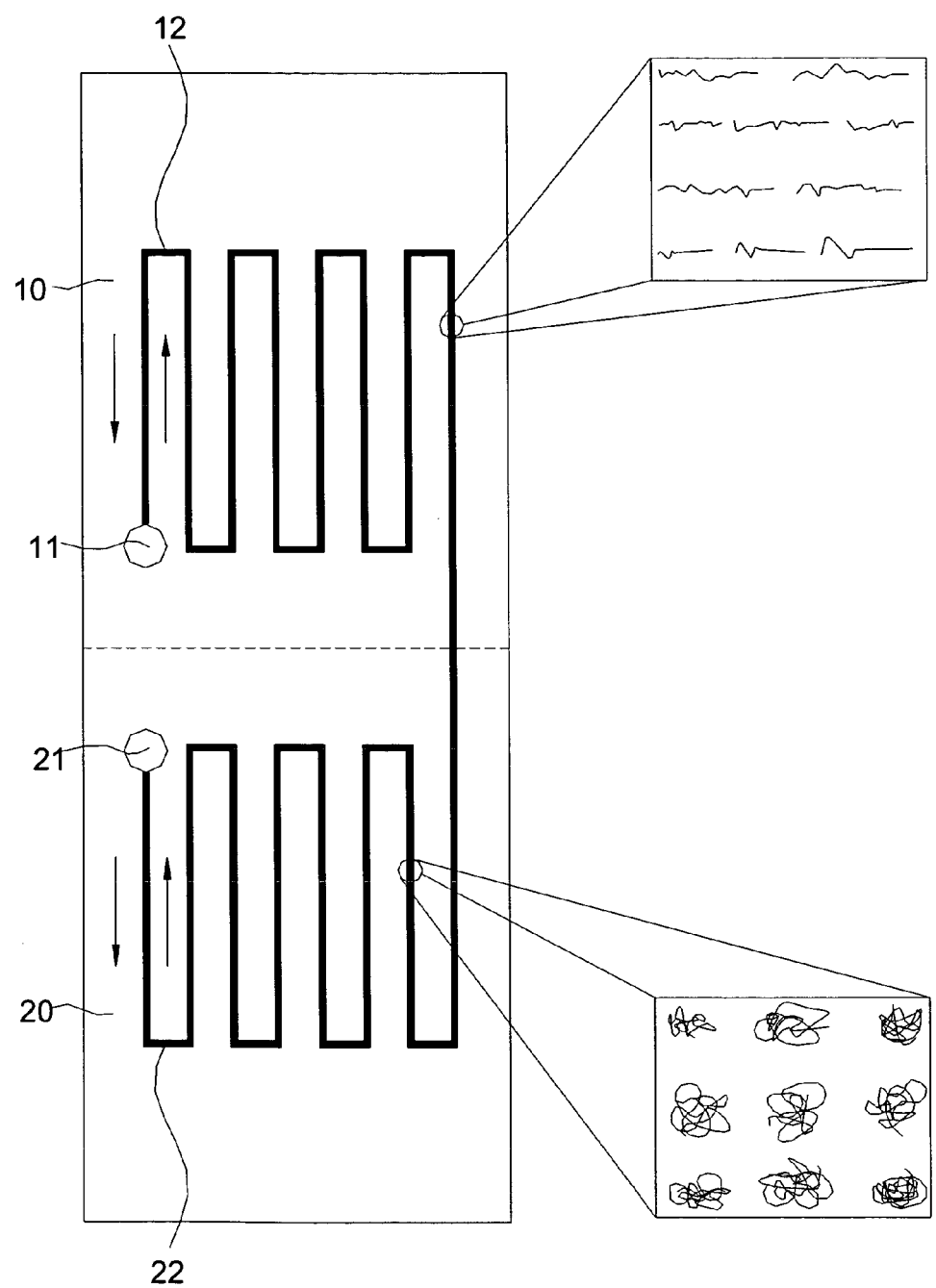
FIG. 1 is a diagram of the nucleic acid hybridization method of the invention.

First of all, the operation principal of the invention is to increase the hybridization rate by elevating the kinetic energy and thermal energy of the nucleic acid-containing fluid. To be more specific, the nucleic acid-containing sample is led to flow back and forth, to increases the nucleic acid extraction rate. Besides, together with an increase in thermal energy to break the intramolecular hydrogen bond of nucleic acid molecules, originally curled nucleic acid molecules become linear and therefore favorable for hybridization.

Based on the foregoing principles, the invention discloses a method with two different nucleic acid reaction areas. The first area is a nucleic acid hybridization area and the second area is a hydrogen bond denaturation area. The temperature of the hydrogen bond denaturation area is higher to denature the intramolecular hydrogen bond of nucleic acids. The temperature of the nucleic acid hybridization area is lower, and in this area the heated linear nucleic acid can cross-hybridize with complementary nucleic acid probes to accelerate hybridization rates. Besides, an element is used to drive fluid back and forth and increase the kinetic energy of the fluid. The kinetic energy of the nucleic acid in the nucleic acid hybridization area can then be increased by continuing back and forth flow. Therefore, hybridized nucleic acid can gain kinetic energy and thermal energy to accelerate the hybridization rate, which is the purpose of the invention.

Consequently, the nucleic acid hybridization method of the invention includes cycles of two stages. The first one is for increasing the thermal energy of nucleic acid molecules and denaturing intermolecular hydrogen bonds of nucleic acids. After completing this stage, the next stage, i.e. the nucleic acid hybridization stage, is processed. In the nucleic acid hybridization stage, through the rapid back and forth flow of samples (containing nucleic acid with a denatured hydrogen bond) to rapidly react with immobilized nucleic acid probes in this area, rapid hybridization can be accomplished. For this reason, the period for samples to stay in the hydrogen bond denaturation area can be only long enough for complete denaturation of the hydrogen bond. Adequate time is allotted for samples to stay in the nucleic acid hybridization area to allow existing nucleic acid molecules with a denaturing hydrogen bond to properly react. After arriving at the nucleic acid hybridization area of lower temperature, nucleic acid molecules with denatured hydrogen bonds are gradually restored back to their original status. Therefore, these two stages have to be processed repeatedly until the desired level of nucleic acid hybridization has been achieved.

Numerous nucleic acid probes are easily immobilized due to their molecular structure, which is able to bind to glass substrates. Immobilized nucleic acid probes can rapidly react with samples containing target nucleic acid (with denatured hydrogen bonds) flowing back and forth. The back and forth flowing rate of the sample can be easily controlled by the element responsible for the flow of fluid. This element can be driven by a two-way pump, either air-driven or fluid-driven. Practically, two-way air-driven mode is better. The back and forth flow rate in the nucleic acid hybridization area can be between 0.1 to 50 rounds per second.

The period of the first stage, which is for the sample to stay in the hydrogen bond denaturation area, can be about 10 seconds, and depends on the inner channel diameter of the hydrogen bond denaturation area. For the second stage, with samples staying in the nucleic acid hybridization area, the period can be about 3 minutes or shorter. The temperature in the hydrogen bond denaturation area can be controlled to around 80-100° C., at which point intramolecular hydrogen bonds of nucleic acids can be denatured; 90° C. is optimal. For the nucleic acid hybridization area, the temperature is between 20 to 68° C., with 40° C. being optimal.

As shown in FIG. 1, the method includes introducing nucleic acid-containing samples from infusion holes 11 or 12 in the hydrogen bond denaturation area, though infusion hole 11 is superior. Through this step, samples can be heated to reach a higher temperature to unfold the nucleic acid and make it linear. A wiggled channel 12 is located in the hydrogen bond denaturation area 10. Since this invented method increases kinetic and thermal energy in the nucleic acids, the size of the channel is not limited. Therefore, the channels can be made in macro- or micro-scale, as well as unlimited shapes.

Similarly, the infusion hole 21 and the wiggled channel 22 are available in the nucleic acid hybridization area 20. As shown in FIG. 1, the channel 22, located in the nucleic acid hybridization area 20, is interconnected with the channel 12, located in the hydrogen bond denaturation area. This interconnection enables the back and forth flows of samples inside the channel. Likewise, shape or size of the channel 22 is not limited. In the nucleic acid hybridization area 20, the surface of the channel 22 is immobilized with lots of nucleic acid probes. When those nucleic acids, which are linearlized by thermal energy, increase, flow to the channel surface area where nucleic acid probes are immobilized, hybridization between nucleic acid and probe occurs. Together with back and forth flow to increase the kinetic energy of samples passing probes, the hybridization rate is synergistically accelerated.

Immobilization of nucleic acid probes on a substrate is by way of affinity between the macromolecule base of the probes and the substrate. Basically, the ability to be immobilized with probes is the selection criteria for the substrate.

According to the above-mentioned protocol, the invention discloses an apparatus for nucleic acid hybridization. Please refer to FIG. 2, which includes a micro-pump 40, a valve element 30, a hydrogen bond denaturation area 10, a nucleic acid hybridization area 20 and a temperature control element 50. Among them, the first channel and the second channel are located in the hydrogen bond denaturation area and nucleic acid hybridization area, respectively. These two channels are interconnected to become a connection channel with the first and second open holes, respectively, and are used for sample influx and as entrance and exit in driving the back and forth flow of fluid.

Figure 2:
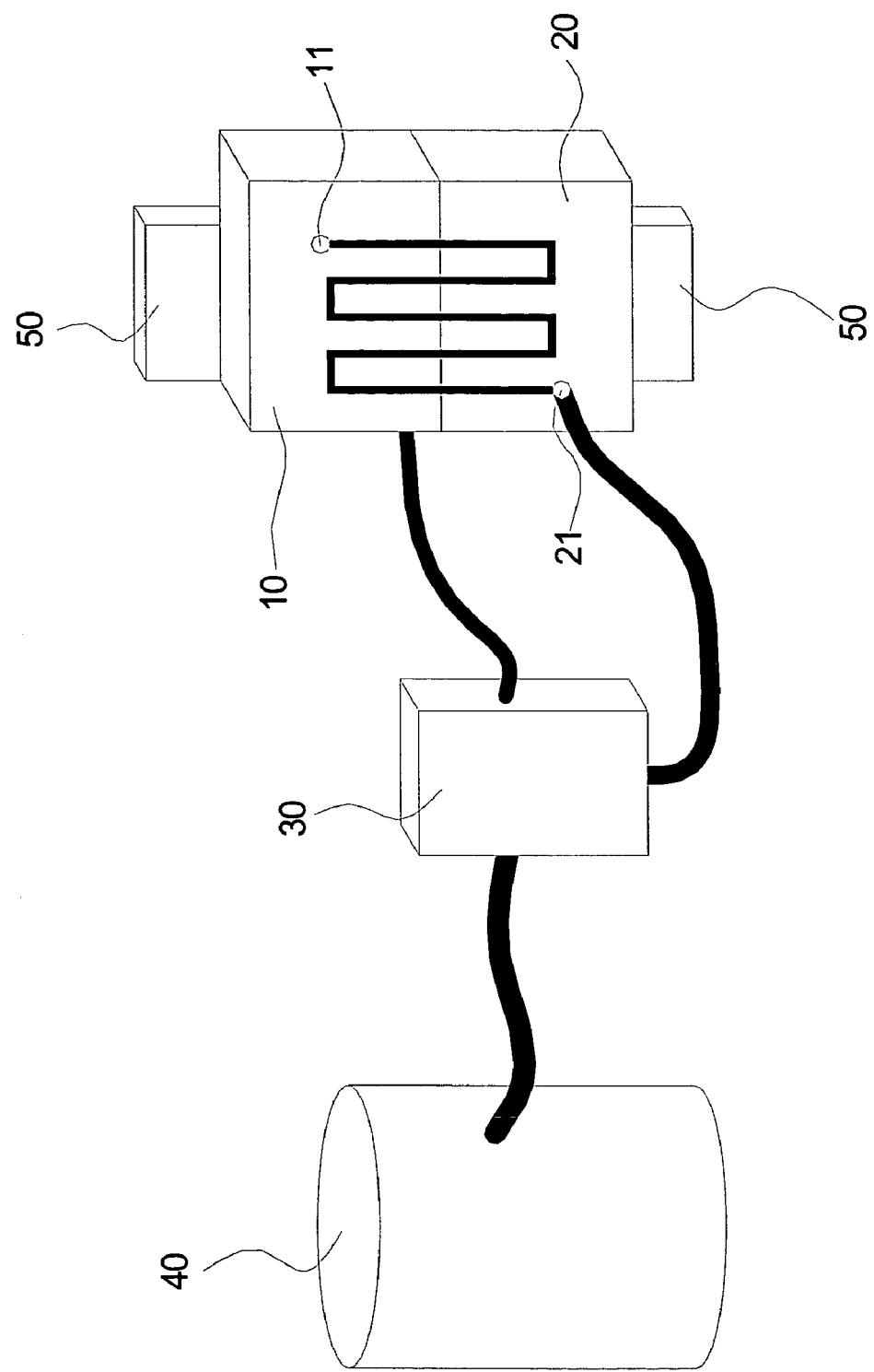
FIG. 2 is a diagram of the nucleic acid hybridization apparatus of the invention.

As shown in FIG. 2, the above-mentioned kinetic energy is provided by micro-pump 40, including transfer of nucleic acid-containing samples from the hydrogen bond denaturation area 10 to the nucleic acid hybridization area 20 and the back-and-forth swift flow of samples inside the channel of the nucleic acid hybridization area 20. The valve element 30 functions to control the flow direction of the micro-pump 40 and then drive the samples to flow from the hydrogen bond denaturation area 10 to the nucleic acid hybridization area 20, or from the nucleic acid hybridization area 20 to the hydrogen bond denaturation area 10. This valve element 30 can also be integrated into the micro-pump 40.

A two-way pump can be used as the micro-pump 40. After the samples inside the hydrogen bond denaturation area have gained enough thermal energy, and nucleic acids in samples have been linearlized, the samples are allowed to flow to the nucleic acid hybridization area 20. Meanwhile, the micro-pump 40 is controlled to repeatedly provide trace kinetic energy to enable existing samples to flow back and forth. Such assistance provided by the micro-pump 40 makes the nucleic acid hybridization of the invention even more efficient.

In the invention, nucleic acid probes applicable in hybridization can be DNA, RNA, peptide, peptide-RNA complex or derivatives of peptide-RNA complex. The temperature control element 50 can maintain a stable temperature for the hydrogen bond denaturation area 10 and the nucleic acid hybridization area 20. An electric heater, microwave, laser, or light can be used as the heat source.

The period for hybridization can be shortened from the 4 hours of original techniques to within 30 minutes, or even shorter, by applying the nucleic acid hybridization method and apparatus of the invention. In theory, it can be shortened to be less than 10 minutes.

The nucleic acid hybridization method and apparatus of the invention is simply constructed, inexpensive and an initiative element is not needed.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A nucleic acid hybridization method, comprising the steps of:
   providing a nucleic acid hybridization area at a first temperature, wherein the nucleic acid hybridization area has a first channel and the surface of the first channel is immobilized with a plurality of probes;
   providing a hydrogen bond denaturation area at a second temperature higher than the first temperature, wherein the bond denaturation area has a second channel and the second channel is interconnected to the first channel to form a connection channel;
   guiding a nucleic acids-containing fluid into the connection channel; and
   driving the nucleic acids-containing fluid to flow in the connection channel back and forth.

2. The nucleic acid hybridization method of claim 1, wherein the first temperature is between 20 to 68° C.

3. The nucleic acid hybridization method of claim 1, wherein the optimal temperature of the first temperature is 40° C.

4. The nucleic acid hybridization method of claim 1, wherein the second temperature is between 80 to 100° C.

5. The nucleic acid hybridization method of claim 1, wherein the optimal temperature of the second temperature is 90° C.

6. The nucleic acid hybridization method of claim 1, wherein the step of driving the nucleic acids-containing fluid comprises driving the nucleic acids-containing fluid utilizing a two-way driving apparatus.

7. The nucleic acid hybridization method of claim 6, wherein the two-way driving apparatus is selected from the group of a two-way air-driven pump and a two-way fluid-driven pump.

8. The nucleic acid hybridization method of claim 1, wherein the step of guiding the nucleic acids-containing fluid comprises guiding a nucleic acids-containing fluid into the connection channel from one of the hydrogen bond denaturation area and the nucleic acid hybridization area.

9. The nucleic acid hybridization method of claim 1, wherein the step of driving the nucleic acids-containing fluid comprises restraining the nucleic acids-containing fluid in the first channel for a first period; driving the nucleic acids-containing fluid from the first channel to the second channel; and restraining the nucleic acids-containing fluid in the second channel for a second period.

10. The nucleic acid hybridization method of claim 9, wherein the step of restraining the nucleic acids-containing fluid in the first channel for the first period comprises driving the nucleic acids-containing fluid utilizing a two-way driving apparatus to flow in the first channel back and forth.

11. The nucleic acid hybridization method of claim 8, wherein guiding a nucleic acids-containing fluid into the connection channel is from the hydrogen bond denaturation area.

12. The nucleic acid hybridization method of claim 9, wherein the step of driving the nucleic acids-containing fluid further comprises driving the nucleic acids-containing fluid from the second channel to the first channel.

\* \* \* \* \*